US007244247B1

(12) United States Patent
Falciani et al.

(10) Patent No.: US 7,244,247 B1
(45) Date of Patent: Jul. 17, 2007

(54) BAG FOR PRESERVING AND TRANSPORTING STERILE PRODUCTS IN POWDER FORM AND FOR FORMING SOLUTIONS OF SAID PRODUCTS IN THE BAG

(75) Inventors: Marco Falciani, Milan (IT); Sergio Dusci, Tresivio (IT)

(73) Assignee: ACS Dobfar S.p.A., Tribiano (IT)

( * ) Notice: Subject to any disclaimer, the term of this patent is extended or adjusted under 35 U.S.C. 154(b) by 429 days.

(21) Appl. No.: 09/807,413

(22) PCT Filed: Apr. 23, 1999

(86) PCT No.: PCT/EP99/02745

§ 371 (c)(1),
(2), (4) Date: Apr. 19, 2001

(87) PCT Pub. No.: WO00/23036

PCT Pub. Date: Apr. 27, 2000

(30) Foreign Application Priority Data

Oct. 20, 1998 (IT) .............................. MI98A2256

(51) Int. Cl.
*A61B 19/00* (2006.01)

(52) U.S. Cl. ................ 604/408; 604/415; 128/DIG. 24

(58) Field of Classification Search ................ 604/408, 604/415, 416; 128/DIG. 24; 222/206; 206/438
See application file for complete search history.

(56) References Cited

U.S. PATENT DOCUMENTS 2,281,473 A * 4/1942 Brewer ........................ 206/438
3,647,386 A * 3/1972 Gilford ........................ 436/179
3,726,276 A * 4/1973 Schumann et al. ........... 604/92
4,282,863 A * 8/1981 Beigler et al. .............. 206/219
4,550,825 A * 11/1985 Sutryn et al. ............... 206/222
4,700,838 A * 10/1987 Falciani et al. ............. 206/438
4,910,147 A 3/1990 Bacehowski et al.
4,968,624 A 11/1990 Bacehowski et al.
5,000,314 A * 3/1991 Fuller et al. ................ 206/221
5,088,996 A * 2/1992 Kopfer et al. .............. 604/415
5,257,986 A * 11/1993 Herbert et al. .............. 604/416
5,364,384 A 11/1994 Grabenkort et al.
5,385,564 A * 1/1995 Slater et al. ................ 128/898
5,484,431 A * 1/1996 Scharf et al. ............... 604/403
6,352,585 B1* 3/2002 Diesso ........................ 106/35
6,695,901 B2* 2/2004 Diesso ........................ 106/35
2002/0128628 A1* 9/2002 Fathallah

FOREIGN PATENT DOCUMENTS

| | | |
|---|---|---|
| HU | 210 255 | 3/1995 |
| HU | 216 090 | 4/1999 |

* cited by examiner

*Primary Examiner*—Alfred Basichas
(74) *Attorney, Agent, or Firm*—Oblon, Spivak, McClelland, Maier & Neustadt, P.C.

(57) ABSTRACT

A bag for preserving and transporting a sterile product in powder form and a method for preparing solutions of the sterile product in the bag. The bag contains a sterile product in powder form and has a port closed by a membrane through which a solvent can be fed into the bag to form a sterile solution of the powder. Further, the bag contains an amount of the sterile product in powder form adapted to give with the solvent and within the bag a reconstituted ready to use solution that only partially fills a capacity of the bag.

9 Claims, 2 Drawing Sheets

BAG FOR PRESERVING AND TRANSPORTING STERILE PRODUCTS IN POWDER FORM AND FOR FORMING SOLUTIONS OF SAID PRODUCTS IN THE BAG

BACKGROUND OF THE INVENTION

1. Field of the Invention

The invention relates to a bag able to preserve a product in powder form under sterile conditions and to enable a liquid to be fed into the bag to form therein a sterile solution of the product.

2. Description of the Background

Many products obtained in sterile form in the solid state are known to be used in the liquid state as sterile solutions, suspensions, dispersions, or the like.

A typical example is a pharmaceutical product such as an antibiotic or vitamin, or a culture medium for micro-organisms such as cells, bacteria or moulds which at the moment of use are dissolved or dispersed in liquid.

The problem of dissolving or dispersing a sterile powder in liquid while maintaining sterility is considerable and costly, and is solved in various ways, all involving problems which are summarized below by referring to two particularly important cases.

For example, cell culture medium is produced in the form of powder which can be sold as such in polyethylene bags or bottles closed with a screw stopper. To be used, this product is dissolved in liquid to form a solution (typically an amino acid, electrolyte or vitamin solution) in a totally septic environment, this involving time and considerable cost.

The sterile solution obtained in this manner is fed into a glass jar or bottle in a suitable sterile bottling environment, and the sealed bottle is despatched to the client in a special housing and protection container. The user has then to open the bottle under aseptic conditions to be able to then withdraw the solution contained in it.

This method is well known, and is explained for example in lines 9–59 of column 1 of the U.S. Pat. No. 4,910,147.

To solve these problems, U.S. Pat. No. 4,910,147 proposes to sell to the user not the product, but instead an already prepared sterile solution of the cell culture medium enclosed in a sealed flexible bag, into which the solution is fed using semi-automatic aseptic filling machines. Such bags, which are completely filled with the solution, are much more manageable than glass bottles and can be easily and economically despatched by the producer to the user who, without the need for a special apparatus or a sterile environment, can directly withdraw all or part of the sterile solution through one or more ports with which the bag is provided.

However, this system also presents problems because although it is relatively simple to store and transport small bags filled with liquid, in the case of bags containing a relatively large liquid volume, for example five liters or more, the hydraulic force exerted by the liquid during transport can break the bag, as is clearly explained in lines 34–50 of column 1 of U.S. Pat. No. 4,968,624, which names the same inventors and the same proprietor as U.S. Pat. No. 4,910,147.

For this reason U.S. Pat. No. 4,968,624 describes a very complex rigid structure within which the bags containing the solutions have to be enclosed for their storage and transport.

Again for example, reference can be made to the method of using those sterile crystalline antibiotics (in powder form) contained in single-dose form in glass bottles sealed by rubber plugs. To make such antibiotics injectable into a patient by using a syringe a sterile solvent (water) is drawn from a vial (which firstly is broken or opened), then the solvent is fed into the bottle by piercing its plug with the syringe needle, the bottle is shaken to dissolve the antibiotic powder, and the solution formed in this manner is drawn into the syringe through the needle which passes through the plug of the bottle, after which the solution can be injected into the patient.

Although this operation may be relatively simple to carry out by a user who has to prepare the solution and inject it only one or a few times a day, it becomes very demanding and costly in hospitals in which specialized personnel (nurses) have to repeat the same operation a very large number of times every day, with considerable time wastage, high cost and serious problems of maintaining sterility, these being enhanced by the need to dispose of a large number of empty glass bottles with rubber plugs, glass vials and miscellaneous packaging material.

Again it should be noted that it is not possible to prepare solutions of antibiotics (for example in bags such as those described in U.S. Pat. No. 4,910,147 and in U.S. Pat. No. 5,364,384) in suitable plants to then despatch them to hospitals, because such solutions remain unaltered only for a very short time, and then only if special care is taken for their preservation.

In order to solve the above mentioned problems the U.S. Pat. No. 5,484,431 has proposed the use of a bag constructed from a flexible polyolefin material, sealed at its periphery and defining a closed sterile space containing a sterile solute or a soluble product in powder form occupying only a minor portion of the capacity of the bag.

The bag has a plurality of ports through which a liquid can be introduced into it for dissolving the powder or solute and respectively for withdrawing the solution which has been formed within the bag.

According to the teachings of the U.S. Pat. No. 5,484,431 the amount of liquid introduced into the bag is such to completely fill it as it is stated, for example, in line 62 of col. 8 and line 23 of col. 9 of the patent specification: in order to make it possible to dissolve the powder or solute contained therein, the bag must include internal means for creating turbulence within its interior (see lines 1–3 of col. 3): preferably the bag is provided with an internal seal 14 (see lines 43–45 and 56–60 of col. 4) which functions to create turbulence when the liquid flows into the bag ensuring an adequate mixing of the liquid and the powder or solute in order to create a solution.

Such solutions are for intravenous administration of dextrose solutions, saline, lactated Ringer's or the like whose concentrations in the respective solutions need not be exactly predetermined and the same in each bag.

The structure of the bag disclosed in the U.S. Pat. No. 5,484,431 is not a simple one, because it must comprise internal means for creating turbulence within its interior as a consequence of the fact that the liquid introduced therein completely fills the bag, so that a simple shaking of the bag would practically be ineffective to completely dissolve the powder or the solute. Moreover, since the bags are formed with a flexible sheet of plastic materials and the bags are completely filled with the liquids introduced therein, it is impossible to obtain solutions all having the same preestablished concentration of the materials dissolved therein.

Finally, the solutions formed in the bags are used for intravenous administration, where it is not necessary to exactly control the amount of the active substances which are administered to the patients.

SUMMARY OF THE INVENTION

In the light of the aforegoing, the main object of this invention is to provide a bag of simple structure usable for preserving and transporting sterile products in powder form and for feeding into it a solvent to easily and quickly form a solution with predetermined concentration of the powdered product directly within the bag under sterile conditions, the bag being provided with at least one port through which the entire solution or a part thereof can be easily, quickly and safely withdrawn in order to be used, the volume of the solution being sufficiently large to supply a plurality of single individually usable doses of the same solution, for example for filling a plurality of syringes.

A further object is to provide a method which enables sterile products in powder form to be packaged in easily storable and transportable flexible bags, and further enables solutions with predetermined concentrations of such products to be subsequently easily and quickly formed directly within the bags when the solution is to be used.

These and further objects are attained by a bag for preserving and transporting sterile products in powder form and for forming therein solutions with predetermined concentrations of the products, the bag being of polyolefins construction, being hermetically sealed at its periphery to define a sterile closed space and having at least one port also of polyolefin construction defining a passageway, the two ends of which open inside and respectively outside the bag. The passageway is closed by a pierceable membrane for the introduction of a solvent into the bag and respectively for the withdrawal of the solution therefrom. The bag contains an amount of product in powder form adapted to give with the solvent and within the bag the reconstituted ready to use solution only partially filling a capacity of the bag capacity, and the total amount of the solution can be a multiple of single volumes of individual doses of the same solution The invention concerns also a bag constructed of flexible polyolefin material and containing a ready to use solution prepared by introducing within a sealed bag originally containing a dosed amount of a soluble sterile product in powder form an amount of solvent adapted to give the ready to use solution with desired concentration of the product. The bag capacity is such that it is only partially filled by the ready to use solution, and the total volume of the solution can be a multiple of single volumes of individual doses of the same solution.

Finally, the invention concerns a method for preparing solutions with predetermined concentrations of soluble sterile products in powder form enclosed and sealed within sterile bags constructed of flexible polyolefin materials, wherein the bag containing a dosed amount of soluble sterile product in powder form adapted to give a solution of predetermined concentration is fed with an amount of solvent adapted to give a ready to use solution with desired concentration of the product, the bag capacity is such that it is only partially filled by the solution, and the volume of the solution suffices to supply a plurality of single individual doses of the same solution.

BRIEF DESCRIPTION OF THE DRAWINGS

The bag structure and its method of use will be more apparent from the ensuing description of a preferred embodiment thereof given by way of non-limiting example with reference to the accompanying drawings, in which.

DISCUSSION OF THE PREFERRED EMBODIMENTS

Figure 1:
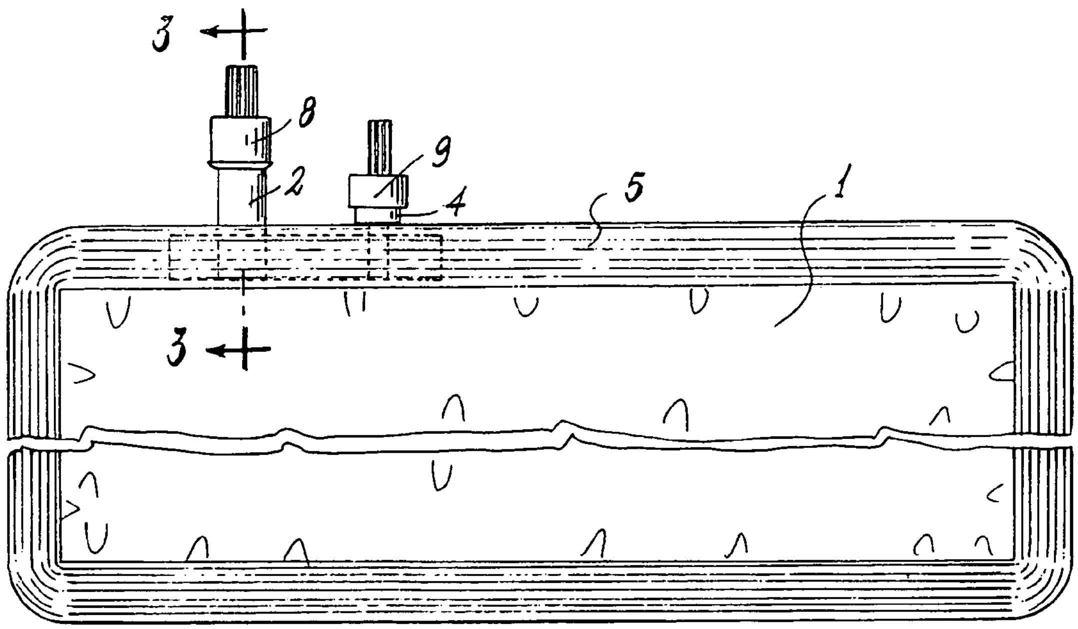
FIG. 1 is a schematic front view of the bag.

Reference will firstly be made to FIGS. 1 to 4, which show a bag 1 constructed of polyolefin, preferably low density polyethylene, sealed hermetically along its entire periphery and having at one end a port 2 formed in one piece with and projecting from an elongate tapered body 3 from which there projects a further port 4. The ports 2 and 4 and the body 3 are constructed of the same material as the bag 1, the body 3 being incorporated into the peripheral bonding seam 5 of the bag 1 so that one end of the ports 2 and 4 opens inside the bag whereas their other end opens outside the bag.

Figure 2:
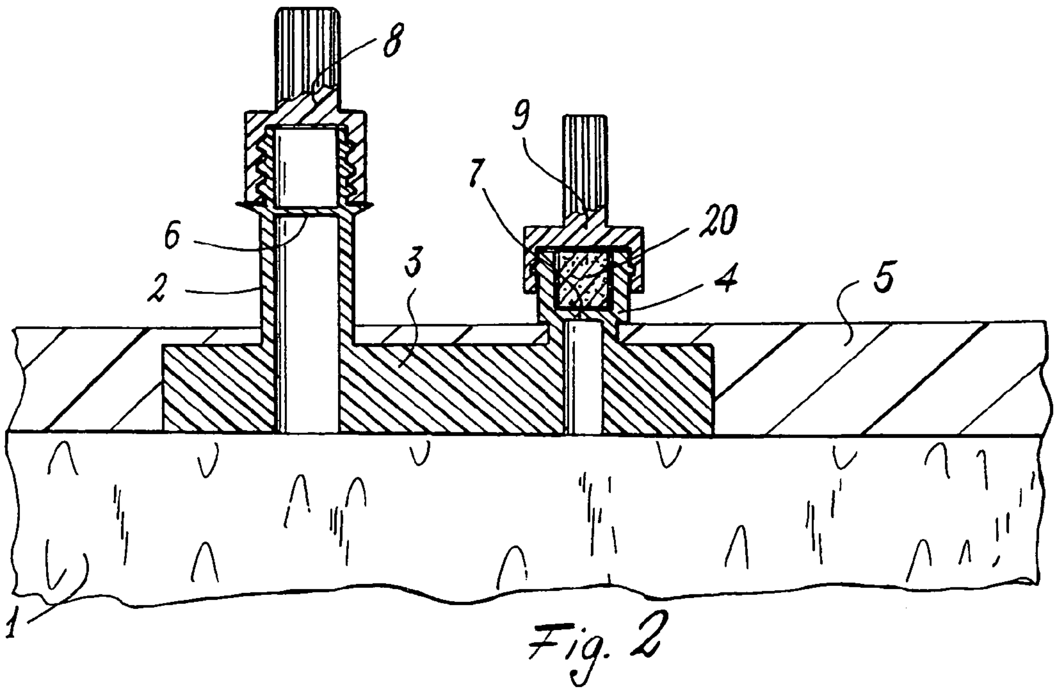
FIG. 2 shows an enlarged partial section coplanar with that portion of the bag on which the bag access port is provided.

As can be seen from FIG. 2 the ports 2 and 4 define conduits closed by respective membranes 6 and 7 respectively, which are formed integrally with the ports and are arranged to ensure sterile conditions in the bag when it contains the product in powder form, as explained hereinafter.

From the figures it can also be seen that on the free ends of the two ports 2 and 4 there are applied protection plugs 8 and 9 respectively, which can be removed if required.

Figure 3:
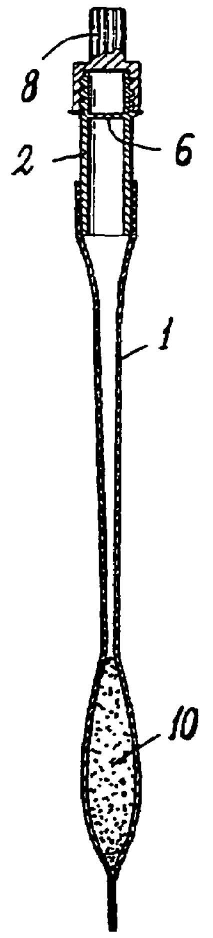
FIG. 3 is a section through the bag taken on the line 3—3 of FIG. 1, the bag being shown filled only to a minimum extent with a product in powder form and with the port closed.

Before bonding the bag 1 along its entire periphery it is sterilized (for example with β rays), then into it, using an automatic machine in a sterile environment, there is fed a mass of sterile product in powder form 10 which, as can be seen from FIG. 3, occupies only a small part of the bag capacity. The powder can be advantageously fed through that end of the bag distant from the end comprising the ports 2 and 4, after which this end is heat-bonded.

The described bag encloses and protects in a sterile environment the sterile product in powder form contained in it.

This bag can be easily and economically stored and transported to the user by the producer who has packaged it.

Figure 5:
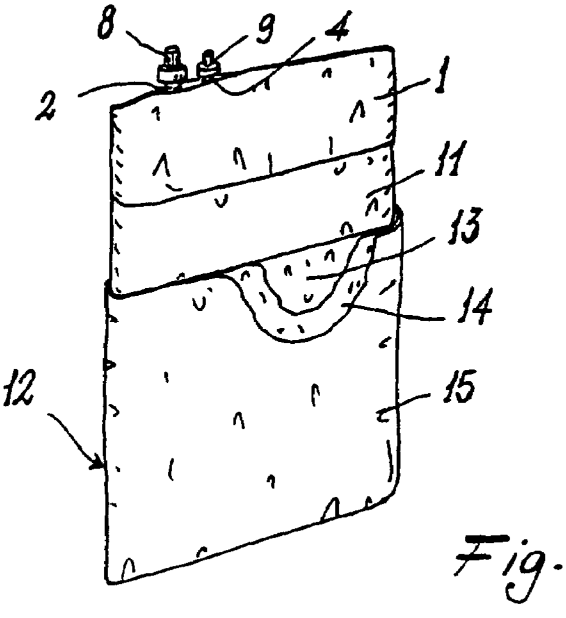
FIG. 5 shows the closed bag inserted into a further two bags used for its storage and its despatch to the powdered product user.

To make storage and transport very secure, the described bag 1 is preferably inserted into an intermediate bag 11 (FIG. 5) also constructed of polyolefin, preferably high density polyethylene, and which after being sealed is inserted into an outer bag 12 composed of three layers of different materials welded together, of which the inner layer 13 is constructed of polyolefin (preferably high density polyethylene) or polyvinyl chloride, the intermediate layer is constructed of a barrier material (preferably aluminium), and the outer layer is constructed of polyolefin, nylon or polyester.

The packaging of the bag 1 in the bags 11 and 12 is known, and is of the type illustrated in U.S. Pat. No. 4,700,838, corresponding to EP-B-201880.

The nature of the barrier material in its general terms (additional to aluminium) can be as defined in U.S. Pat. No. 4,910,147.

Figure 4:
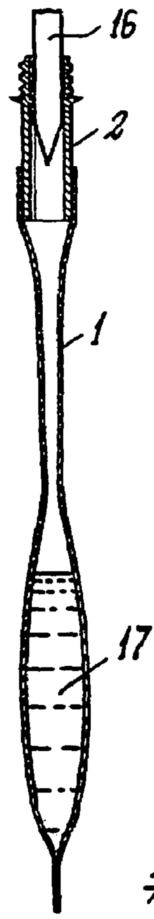
FIG. 4 is similar to FIG. 3, but with the port open for feeding into the bag a liquid having a volume occupying only a part of the bag capacity.

When the sterile product in powder form is to be used, the bag 1 is removed from the protection bags, the plug 8 is unscrewed, and into the port 2 a perfuser is inserted so that its free end 16 fractures the membrane 6 (FIG. 4). The perfuser is a well known device and will not be described for simplicity. Its end sealedly engages the cavity in the appendix 2, through which the desired quantity of water can be easily fed under sterile conditions into the bag 1 to form with the powdered product a solution 17 which fills only a part of the bag capacity. This merely partial filling of the bag 1 not only is necessary to enable the liquid in the bag to be energetically shaken in order to quickly and completely dissolve the product in powder form to make it suitable for use, but it makes it possible to introduce into the bag the exactly controlled amount of liquid which is required for giving a solution in which the product is present at its predetermined concentration.

One of the preferred uses of the described bag is to preserve and transport sterile crystalline antibiotics and to form injectable solutions thereof (in hospitals and the like) in which the concentration of the antibiotics must be carefully controlled; this means that if the amount of an antibiotic closed in a bag is known, also the amount of water to be introduced into the same bag for forming the solution is known.

To give a detailed practical example, a bag 1 is prepared from a sheet of low density polyethylene of 150 micron thickness, the bag having a height of 35 cm and a width of 45 cm. 300 g of an antibiotic in powder form are fed into this bag and preserved in a sterile environment. The bag 1 is sealed within an intermediate bag of high density polyethylene of 100 micron thickness, having a height of 40 cm and a width of 48 cm. The intermediate bag is then inserted into and sealed inside an outer bag of 43 cm height and 54.4 cm width formed from three layers joined together, the inner layer being formed of high density polyethylene of 0.075 mm thickness, the intermediate layer being formed of a sheet of aluminium of 0.01 mm thickness, and the outer layer being of polyester resin of 0.012 mm thickness.

When the antibiotic is to be used, the inner bag 1 is removed from the intermediate bag 11 and outer bag 12 and 3000 ml of injection-quality water are fed into it via the described perfuser (FIG. 4) to form a solution of the required concentration for the particular therapeutic dose, in this case 100 mg/ml. It is important to note that the antibiotic solution 17 occupies only a part of the bag capacity to enable the antibiotic to be quickly and completely dissolved by vigorously shaking the bag. The bag capacity is preferably between 1.5 and 2 times the volume of the solution to be prepared in it.

The antibiotic solution obtained in this manner can be used directly, for example it can be transferred into sterile syringes each containing 30 ml of solution. The syringes can be filled in groups (for example 10, 20 or more syringes at a time) by automatic machines of known type which withdraw the solution through the free end 16 of the perfuser (by arranging the bag with the port 2 pointing downwards) used for feeding the liquid into the bag.

If desired, individual doses of the antibiotic solution can be withdrawn through the port 4 (the presence of which is not strictly necessary but is preferred). To do this, the protection plug 9 is removed, and a rubber plug 20 (which seals that part of the cavity of the port 4 external to the bag 1) and the membrane 7 are perforated by the syringe needle.

When the syringe needle is removed, the solution is unable to flow from the bag 1, this being prevented by the rubber plug 20.

If the syringes are not used within a short time after their filling, they can be preserved in a freezer and then be despatched to the user in hospital in controlled temperature containers.

From the aforegoing description it is apparent that the antibiotic solution can be very easily and quickly formed at the desired concentration in a sterile environment, and that syringes can then be filled likewise easily and economically.

By proceeding in the aforedescribed manner, very important advantages are obtained compared with traditional systems in that it is no longer necessary to preserve the sterile antibiotic in powder form in glass bottles, a considerable reduction in the risk of contamination of the final pharmaceutical product is achieved (with the traditional system, for each syringe the solution has to be prepared individually and be fed into the syringe in environments which are generally not sterile), and there is a considerable cost and ecological saving consequent on the fact that it is no longer necessary to use glass bottles, metal rings, rubber plugs (one for each bottle), glass vials for solvents, etc.

All this leads to a considerable cost reduction, especially because a large number of specialized personnel are no longer required for preparing the individual antibiotic solutions, this being a very costly operation in hospitals or in those places in which a large quantity of antibiotic solutions have to be prepared.

Very considerable advantages are obtained even if the sterile products contained in the bags are not pharmaceutical products but are other products in powder form to be dissolved in various liquids for their use.

In addition to the described bag, the invention also relates to the method for preserving and transporting sterile products in powder form and for dissolving them in liquids under sterile conditions, as defined in the introductory part and in the claims accompanying this description.

The invention claimed is:

1. A method for preparing solutions with predetermined concentrations of soluble sterile product in powder form enclosed and sealed within a sterile bag constructed of flexible polyolefin materials, comprising:

feeding into the bag, containing a dosed amount of soluble sterile product in powder form adapted to give a solution of a predetermined concentration, an amount of solvent adapted to reconstitute a ready to use solution with a desired concentration of the sterile product, a capacity of the bag being larger than a volume of the ready to use solution after the ready to use solution is reconstituted in the bag, and wherein the volume of the ready to use solution reconstituted in the bag is a multiple of single doses of the ready to use solution directly usable for practical utilization; and removing from the bag the reconstituted ready to use solution in individual dose sizes.

2. A method for preparing solutions with predetermined concentrations of soluble sterile product in powder form enclosed and sealed within a sterile bag constructed of flexible polyolefin materials, comprising:

feeding into the bag, containing a dosed amount of soluble sterile product in powder form adapted to give a solution of a predetermined concentration, an amount of solvent adapted to reconstitute a ready to use solution with a desired concentration of the sterile product such that the fed amount of solvent is less than a capacity of the bag, and wherein a volume of the ready to use solution reconstituted in the bag is a multiple of single doses of the ready to use solution directly usable for practical utilization; and removing from the bag the reconstituted ready to use solution in individual dose sizes.

3. A method according to claim 2, wherein the fed amount of solvent is ⅔ to ½ of the capacity of the bag.

4. A method for preparing solutions with predetermined concentrations of soluble sterile product in powder form enclosed and sealed within a sterile bag constructed of flexible polyolefin materials, the bag containing a dosed amount of soluble sterile product in powder form adapted to give a solution of a predetermined concentration, comprising:

feeding into the bag an amount of solvent adapted to reconstitute a ready to use solution with a desired concentration of the sterile product, such that the fed amount of solvent is less than a capacity of the bag and such that a capacity of the bag is larger than a volume of the ready to use solution after the ready to use solution is reconstituted in the bag, and wherein the volume of the ready to use solution reconstituted in the bag is a multiple of single doses of the ready to use solution directly usable for practical utilization; and removing from the bag the reconstituted ready to use solution in individual dose sizes.

5. A method according to claim 4, wherein the fed amount of solvent is ⅔ to ½ of the capacity of the bag.

6. A method for using a sterile bag constructed of flexible polyolefin materials containing a dosed amount of soluble sterile product in powder form adapted to give a solution of a predetermined concentration, comprising:

feeding into the bag, containing a dosed amount of soluble sterile product in powder form adapted to give a solution of a predetermined concentration, an amount of solvent adapted to reconstitute a ready to use solution with a desired concentration of the sterile product such that the fed amount of solvent is less than a capacity of the bag, and wherein a volume of the ready to use solution reconstituted in the bag is a multiple of single doses of the ready to use solution directly usable for practical utilization; and removing from the bag the reconstituted ready to use solution in individual dose sizes.

7. A method according to claim 6, wherein the fed amount of solvent is ⅔ to ½ of the capacity of the bag.

8. A method for using a sterile bag constructed of flexible polyolefin materials, the bag containing a dosed amount of soluble sterile product in powder form adapted to give a solution of a predetermined concentration, comprising:

feeding into the bag an amount of solvent adapted to reconstitute a ready to use solution with a desired concentration of the sterile product, such that the fed amount of solvent is less than a capacity of the bag and such that a capacity of the bag is larger than a volume of the ready to use solution after the ready to use solution is reconstituted in the bag, and wherein the volume of the ready to use solution reconstituted in the bag is a multiple of single doses of the ready to use solution directly usable for practical utilization; and removing from the bag the reconstituted ready to use solution in individual dose sizes.

9. A method according to claim 8, wherein the fed amount of solvent is ⅔ to ½ of the capacity of the bag.

* * * * *